US012778739B2

(12) United States Patent

Duquesnel et al.

(10) Patent No.: US 12,778,739 B2

(45) Date of Patent: Nov. 3, 2026

(54) APPARATUS AND METHOD FOR IMPLANTING BONE ANCHOR UNDER CONTROLLED TENSION

(71) Applicant: Tesa Medical, Inc., San Francisco, CA (US)

(72) Inventors: Brandon Duquesnel, Temecula, CA (US); Brian Bowman, Carlsbad, CA (US); Clayton Alderson, Solana Beach, CA (US); Diana Rosales, Union City, CA (US); Ian Fried, San Diego, CA (US); Howard Edelman, San Francisco, CA (US); Scott Edward Parazynski, Houston, TX (US)

(73) Assignee: Tesa Medical Inc., Chicago, IL (US)

( * ) Notice: Subject to any disclaimer, the term of this patent is extended or adjusted under 35 U.S.C. 154(b) by 803 days.

(21) Appl. No.: 18/300,701

(22) Filed: Apr. 14, 2023

(65) Prior Publication Data

US 2023/0320838 A1 Oct. 12, 2023

Related U.S. Application Data

(63) Continuation of application No. PCT/US2021/055073, filed on Oct. 14, 2021.

(Continued)

(51) Int. Cl.

*A61F 2/08* (2006.01)

(52) U.S. Cl.

CPC .... *A61F 2/0805* (2013.01); *A61F 2002/0829* (2013.01); *A61F 2002/0852* (2013.01);

(Continued)

(58) Field of Classification Search

CPC .................. A61F 2/0805; A61F 2/0811; A61F 2002/0829; A61F 2002/0852;

(Continued)

(56) References Cited

U.S. PATENT DOCUMENTS

| | | | |
|---|---|---|---|
| 6,086,608 A | 7/2000 | Ek et al. | |
| 6,780,198 B1 * | 8/2004 | Gregoire ............ | A61B 17/0401 606/232 |

(Continued)

FOREIGN PATENT DOCUMENTS

WO WO-2022081901 A1 4/2022

OTHER PUBLICATIONS

PCT/US2021/055073 International Search Report and Written Opinion dated Mar. 23, 2022.

*Primary Examiner* — Phong Son H Dang

(74) *Attorney, Agent, or Firm* — Taft Stettinius & Hollister LLP

(57) ABSTRACT

A graft tensioning tool includes an elongate frame having a proximal end, a distal end, and an axial passage extending therethrough. The distal end is configured to detachably engage a tunnel ring at an entrance to a tunnel in bone, and the frame includes a first suture puller and a second suture puller. Each suture puller detachably engages a length of suture emerging through the attached to suture and/or a soft tissue implant in the bone tunnel. A tensioner on the elongate frame displaces the suture pullers in a proximal direction to apply a controlled tension to the suture lengths and/or implant. A tension gauge measures tension applied to the suture pullers, and a locking tool is configured to engage the suture lock through the axial passage of the frame, allowing a user to fix the suture ends to bone when a target tension is attained.

39 Claims, 10 Drawing Sheets

Related U.S. Application Data

(60) Provisional application No. 63/091,731, filed on Oct. 14, 2020.

(52) U.S. Cl.
CPC ................. *A61F 2002/0882* (2013.01); *A61F 2250/0012* (2013.01)

(58) Field of Classification Search
CPC ...... A61F 2002/0858; A61F 2002/0882; A61F 2250/0012; A61B 90/06; A61B 2090/064; A61B 2090/067; A61B 17/0401
See application file for complete search history.

(56) References Cited

U.S. PATENT DOCUMENTS

| | | | | |
|---|---|---|---|---|
| 7,517,357 | B2 | 4/2009 | Abrams et al. | |
| 8,182,495 | B2 | 5/2012 | DiStefano et al. | |
| 8,298,247 | B2 | 10/2012 | Sterrett et al. | |
| 8,939,999 | B2 | 1/2015 | Sterrett et al. | |
| 9,186,133 | B2 | 11/2015 | Gregoire et al. | |
| 9,717,492 | B2 | 8/2017 | Sojka et al. | |
| 9,788,825 | B2 * | 10/2017 | Whittaker | A61B 17/0401 |
| 9,820,793 | B1 | 11/2017 | Wade | |
| 9,943,304 | B2 | 4/2018 | Branthover et al. | |
| 10,390,817 | B2 * | 8/2019 | Bonutti | A61B 17/683 |
| 10,499,900 | B2 | 12/2019 | Wade | |
| 10,499,972 | B2 * | 12/2019 | Bosshard | A61B 17/8869 |
| 2002/0188301 | A1 * | 12/2002 | Dallara | A61B 17/068 606/104 |
| 2005/0049598 | A1 | 3/2005 | West et al. | |
| 2006/0271060 | A1 | 11/2006 | Gordon | |
| 2008/0033460 | A1 * | 2/2008 | Ziniti | A61B 17/0401 606/148 |
| 2009/0287188 | A1 * | 11/2009 | Golden | A61B 1/0052 604/528 |
| 2009/0326562 | A1 * | 12/2009 | White | A61B 17/8869 606/139 |
| 2017/0156779 | A1 | 6/2017 | Bryant et al. | |
| 2020/0155140 | A1 | 5/2020 | Palese | |
| 2020/0281580 | A1 * | 9/2020 | Kruse | A61B 17/0401 |
| 2024/0156586 | A1 * | 5/2024 | Gabel | A61B 17/8869 |
| 2024/0173027 | A1 * | 5/2024 | Le | A61B 17/0487 |

* cited by examiner

APPARATUS AND METHOD FOR IMPLANTING BONE ANCHOR UNDER CONTROLLED TENSION

CROSS-REFERENCE TO RELATED APPLICATIONS

This application is a continuation of PCT Application No. PCT/US21/55073, filed Oct. 14, 2021, which claims the benefit of U.S. Provisional No. 63/091,731, filed Oct. 14, 2020, the entire content of which is incorporated herein by reference.

BACKGROUND OF THE INVENTION

1. Field of the Invention

The present invention relates generally to medical devices, systems, and methods and more particularly to methods and apparatus for tensioning and fixating soft tissue and prosthetic grafts to bone, for example in orthopedic graft reconstruction surgeries, such as anterior cruciate ligament (ACL) repair and other procedures.

ACL reconstruction is commonly performed to restore knee joint function and to decrease the risk of post-traumatic osteoarthritis (OA) in the ACL-injured knee. While the result of ACL reconstruction are generally successful, such procedures still face challenges. For example, the initial tension applied to the graft before fixation affects knee stability and joint contact forces, and an improper initial tension may cause OA.

It can be a difficult to continuously and accurately measure the tension being applied on a distal end of the graft prior to fixation of a proximal end of the graft and, even when the such tension can be accurately assessed, it can be difficult to complete fixation of the proximal end of the graft while maintaining a desired amount of tension.

For these reasons, it would be desirable to provide improved apparatus, systems, and methods for the controlled tensioning, positioning, and fixation of grafts used in ACL and other orthopedic procedures. At least some of these objectives will be met by the inventions described and claimed hereinbelow.

2. Listing of Background Art

U.S. Pat. Nos. 8,298,247 and 8,939,999 describe graft tensioning devices. The INTRAFIX® System for tibial fixation and tensioning for use in ACL repair is commercially available from DePuyMitek, Raynham, MA.

SUMMARY OF THE INVENTION

The present invention provides a graft tensioning tool for use in soft tissue fixation procedures, for example in orthopedic graft reconstruction surgeries, such as anterior cruciate ligament (ACL) repair and other joint reconstruction procedures. A distal end of a tissue graft is attached to a remote bone surface and pulled back through a tunnel formed in an adjacent bone toward a proximal opening the tunnel. A suture is typically attached to the free proximal end of the tissue graft, and two free ends of the suture are pulled through the proximal tunnel opening, and the suture ends are fixed to the tunnel opening to apply an appropriate tension to the graft.

The procedures of the present invention rely on placing a tunnel ring, such as a shoulder washer or "top hat," at the proximal opening of the bone tunnel. A suture lock is secured to the tunnel ring to lock or fix the suture after a desired tension has been applied by a graft tensioning tool. Although the description and claims herein will after refer to fixation of suture, in some cases, at least a portion of the tissue graft itself may be pulled through the tunnel ring and locked in place by the suture lock, either with the suture or in some instances in place of the suture.

In a first aspect of the present invention, the graft tensioning tool comprises an elongate frame having a proximal end, a distal end, and an axial passage extending therethrough. The distal end of the shaft is configured to detachably engage the tunnel ring, and the frame is coupled to a first suture puller and a second suture puller. Each suture puller is configured to detachably engage a length of suture (or in some cases a length of graft), and a tensioner on the elongate frame is configured to displace the first and second suture pullers in a proximal direction relative to the elongate frame. A tension gauge is coupled to the tensioner to measure tension applied by the tensioner to the first and second suture pullers, and a locking tool is configured to engage the suture lock through the axial passage of the frame when the distal end of the frame engages the opening in the tunnel ring.

In some examples, the first suture puller is disposed on a first side of the elongate frame and the second suture puller is disposed on a second side of the tensioner frame. Usually, the first and second suture pullers will be aligned on laterally opposite sides of the frame, but in other instances the suture pullers could be axially staggered, be in tandem on the same side of the frame, or have other configurations which allow for tension to be applied in a proximal direction away from the bone tunnel. The first and second suture pullers will typically be arranged to be pulled in unison but that is not necessary as separate tensioning of the suture lengths, although not preferred, could be implemented.

In the examples herein, the tensioner is configured to displace the first and suture pullers simultaneously.

In some examples, the locking tool is configured to carry the suture lock through the axial passage of the frame and position the suture lock in the opening in the tunnel ring.

In some examples, the distal end of the elongate frame comprises an opening configured to circumscribe the tunnel ring.

In some examples, the tunnel ring has a lower surface configured to engage cortical bone and un upper surface and wherein the opening of the elongate frame is configured to circumscribe the upper surface of tunnel ring.

In some examples, the opening is configured to interlock with the upper surface the tunnel ring. For example, an interlock may include a protrusion on the opening of distal end of the elongate frame and a recess on an exterior surface of the tunnel ring, where the protrusion is configured to engage the recess when the opening circumscribes the tunnel ring.

In some examples, the first and second suture pullers each comprise a cleat.

In some examples, the first and second suture pullers may be mounted on a carriage that is slidably disposed in a distal portion of the passage in the frame, wherein the suture pullers are exposed through slots in the frame. For example, the tensioner may comprise a shuttle assembly coupled to the carriage, wherein the shuttle assembly is configured to be retracted to proximally displace the carriage. The shuttle assembly is typically configured to be manually retracted, but in other instances could be configured to be immortalized or otherwise have a powered operation.

In some examples, the shuttle assembly comprises an externally threaded cylinder and an internally threaded knob, where in knob is rotatably mounted on the frame at a fixed axial position and the threaded cylinder is slidably mounted in the passageway of the frame but prevented from rotating, wherein a proximal portion of the threaded cylinder is received in a distal portion of the knob so that manual rotation of the knob will proximally retract the threaded cylinder. It will be appreciated, of course, that a variety of other shuttle assemblies could be used, such as ratchet assemblies, levered assemblies, and the like.

In some examples, the shuttle assembly may further comprise a spring coupling the threaded cylinder to the puller carriage. In such instances, the tension gauge is typically coupled to the spring to provide a tension readout based upon elongation of the spring.

In other examples, the tension gauge comprises a load cell transducer and the readout comprises a digital display.

In some examples, the graft tensioning tool may further comprise a wireless transmitter connected to the load cell for transmission to a remote digital display. For example, the load cell is wired to a digital display on the elongate frame.

The locking tool may have a variety of structures, typically comprising a shaft with a proximal handle and a distal end configured to detachably engage the suture lock.

The tensioner may be configured to apply a continuously variable tension, such as when a threaded tensioner is used. In other instances, the tensioner may apply an incremental tensioning, such as when a ratcheting retraction mechanism is employed.

The tensioner will typically be configured to displace the first and second suture pullers simultaneously, but in other instances may be configured to displace the pullers separately.

The tensioner is typically configured to displace the first and second suture pullers in both proximal and distal directions relative to the elongate frame, but in some instances could be configured to retract only in a proximal direction, for example if a separate release mechanism is provided to release the tensioner and all tension on the sutures.

In a second aspect, the present invention provides graft tensioning systems comprising the graft tensioning tool as described above in combination with a tunnel ring and a suture lock.

In some examples of the graft tensioning systems, the tunnel ring comprises a shoulder washer. For example, the shoulder washer may have a pair of interior channels on an interior surface for receiving and guiding the suture lengths and, the interior surface may be threaded.

In some examples of the graft tensioning systems, the suture lock comprises a threaded shaft that can be rotatably advanced into the tunnel ring to compress and lock the suture and/or a graft implant.

In a third aspect, the present invention provides a cortical implant comprising a tunnel ring and a suture lock, where the suture lock is configured to be advanced into an interior of the tunnel ring to compress and lock suture and/or a graft implant.

The suture ring lock of the cortical implant typically comprises a locking element configured to compressively engage the suture lock as the suture lock is advanced into the interior of the tunnel ring.

The tunnel ring of the cortical implant typically comprises a threaded passage having a pair of axial suture channels formed therein, and the suture lock typically comprises a threaded shaft configured to be rotatably advanced into the threaded passage to compress and lock the suture.

In a fourth aspect, the present invention provides a method of tensioning a pair of suture ends extending through an opening of a tissue tunnel in bone. The method comprises fixing at least one suture strand to a tissue structure or implant to be tensioned, where the pair of suture ends extends through the opening of the tissue tunnel. A tensioning tool comprising an elongated frame, first and second suture pullers, and a locking tool is provided, a distal end of the elongated frame is engaged against a tunnel ring disposed at the opening of the tissue tunnel. Each of the suture ends is detachably secured to one of the suture pullers, and the suture pullers are drawn in a proximal direction relative to the frame to tension the at least one suture strand. A locking tool is advanced distally through a central passage of the frame to engage a suture lock proximate the tunnel ring, and the suture lock is tightened in the opening of the tunnel ring with the locking tool to lock the suture in place.

When performing such methods, the suture lock may be advanced to the tunnel ring through the central passage of the frame by the locking tool.

When performing such methods, the suture lock may be placed in the opening of the tunnel ring prior to engaging the distal end of the elongated frame against the tunnel ring.

Such methods may further comprise determining an amount of tension exerted on the suture while the drawing the suture pullers, wherein the suture lock is positioned and coupled to the tunnel ring when the amount of tension is at target value or within a target range.

Such methods may further comprise displaying the amount of tension to allow monitoring by a user while the user is manually drawing the suture pullers.

When performing such methods, fixing the at least one suture strand may comprise attaching the suture strand directly or indirectly to a prosthetic joint graft.

When performing such methods, engaging the distal end of the elongated frame against the tunnel ring may comprise circumscribing an upper opening of the tunnel ring to align the central passage of the elongated frame with said upper opening.

When performing such methods, detachably securing each of the suture ends to one of the suture pullers may comprise securing the suture ends to a pair of cleats on opposite side of the frame. For example, the cleats may be coupled to a carriage slidably mounted in the central passage of the frame, and the suture pullers may be drawn in a proximal direction by pulling the carriage proximally through the central passage. For example, drawing the carriage proximally through the central passage may comprise rotating a knob that is threadably coupled to the carriage.

In a specific instance, the tunnel ring may have a threaded interior surface with channels for receiving the suture ends and the suture lock comprises a threaded shaft, and coupling the suture lock to the tunnel ring may comprise rotatably inserting the threaded shaft into the tunnel ring to compress and lock the suture in place.

Such methods may further comprise determining and an angle of flexion of a joint during performance of the procedure. Such methods may further comprise observing an amount of tension exerted on the suture at different angles of flexion, allowing the user to lock the suture in place when a target amount or range of tension is observed.

In other aspects, the present invention provides a graft tensioning system comprising a top hat configured to be placed in an entrance into a bone bore. A frame has a proximal end and a distal end, where the distal end is configured to engage the passage in the top hat. A graft tightening assembly disposed on the frame includes a first suture puller on a first side of the tensioner frame and a second suture puller on a second side of the tensioner frame. A variable load transfer element is attached to a proximal end of the graft tightening assembly, and a tensioner on a proximal portion of the frame is configured to apply a controlled proximal tension on a proximal end of the variable load transfer element. A read out on the frame shows the magnitude of tension being applied by the tensioner to the graft tightening assembly.

In specific embodiments, the variable load transfer element comprises a spring and the readout may comprise a scale coupled to the spring. In alternative embodiments, the variable load transfer element may comprise a load cell transducer and the readout may comprise a digital display. In either embodiment, the digital display shows both tension and angle.

In other embodiments, the graft tensioning system of the present invention may further comprise a lock configured to threadably engage the top hat to secure suture to the top hat, optionally further comprising a lock driver having a distal end configured to removably carry the lock. Typically, the frame will have a central passage extending axially therethrough where the lock driver is rotatably received in the central passage with the lock positioned distally of the distal end of the frame.

In still other embodiments, the frame further may comprise a pair of guide channels at the distal end of the frame. The guide channels may taper in a distal direction to form a distal tip which engages with the top hat. The lock driver may be configured to advance the lock through the distal tip formed by the channels and into the top hat, and the tensioner may comprise a threaded knob on a proximal portion of the frame.

DETAILED DESCRIPTION OF THE INVENTION

Figure 1:
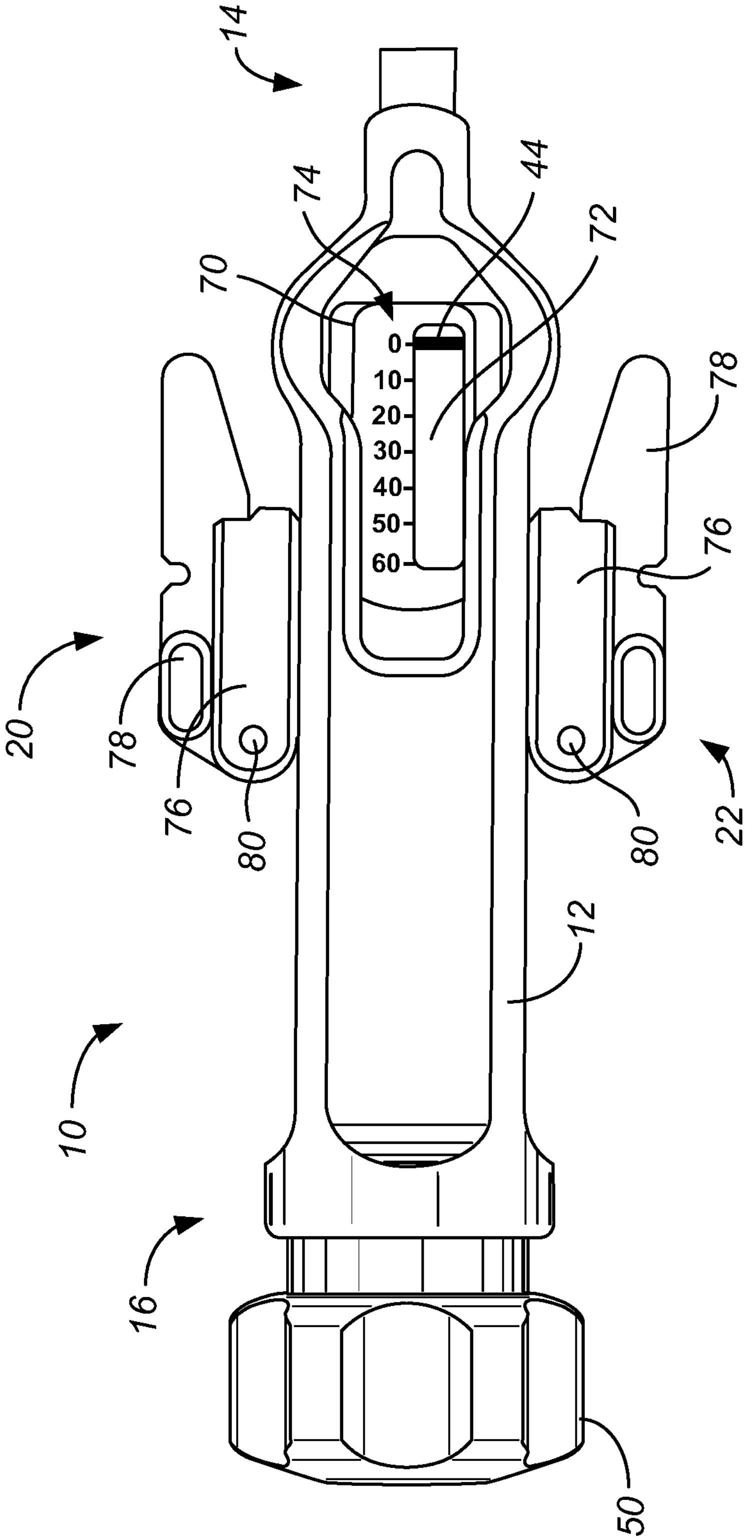
FIG. 1 is a top view of a graft tensioning tool constructed in accordance with the principle of the present invention.
Figure 2:
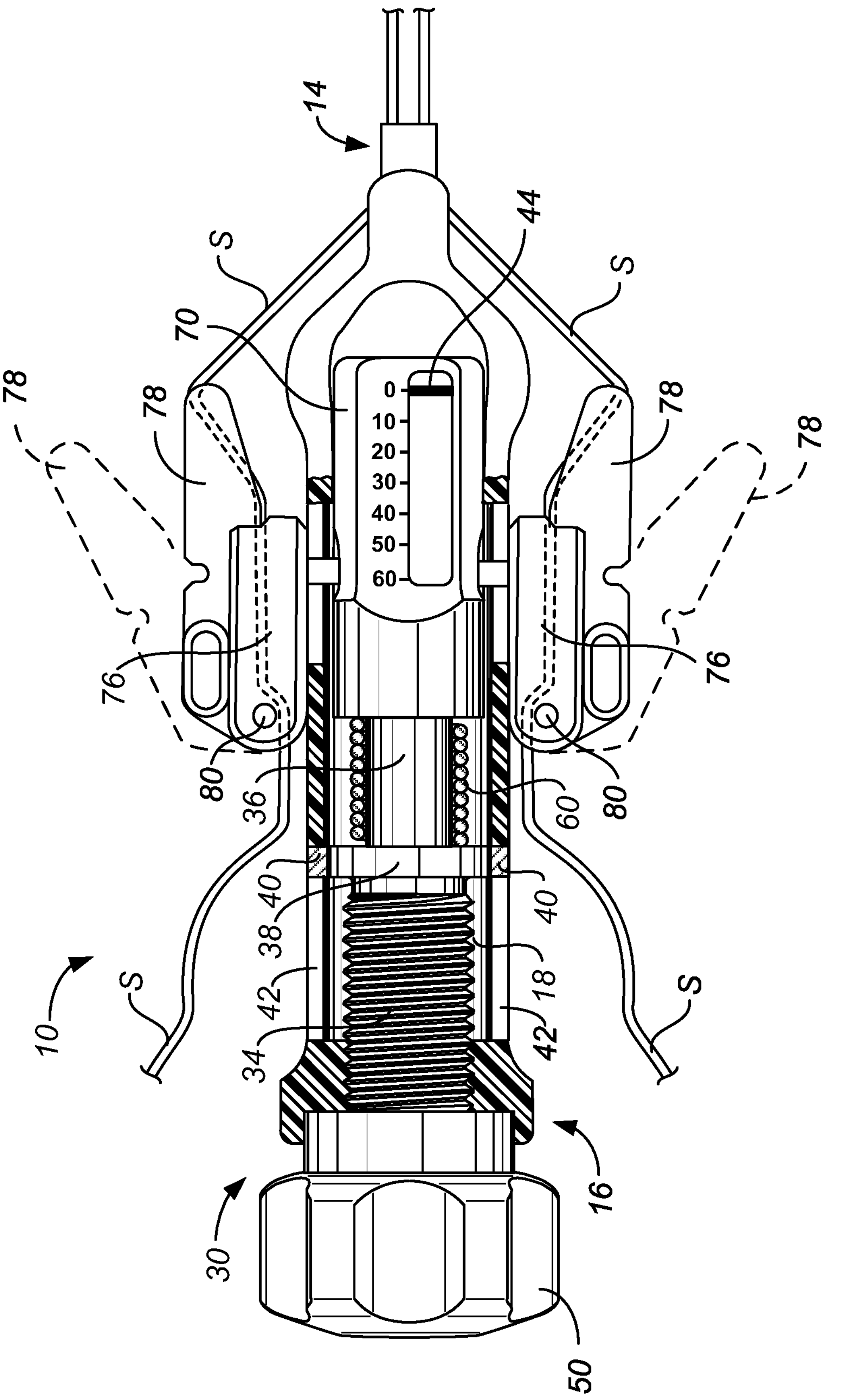
FIG. 2 is a top view of the graft tensioning tool of FIG. 1 shown with portions broken away.
Figure 3:
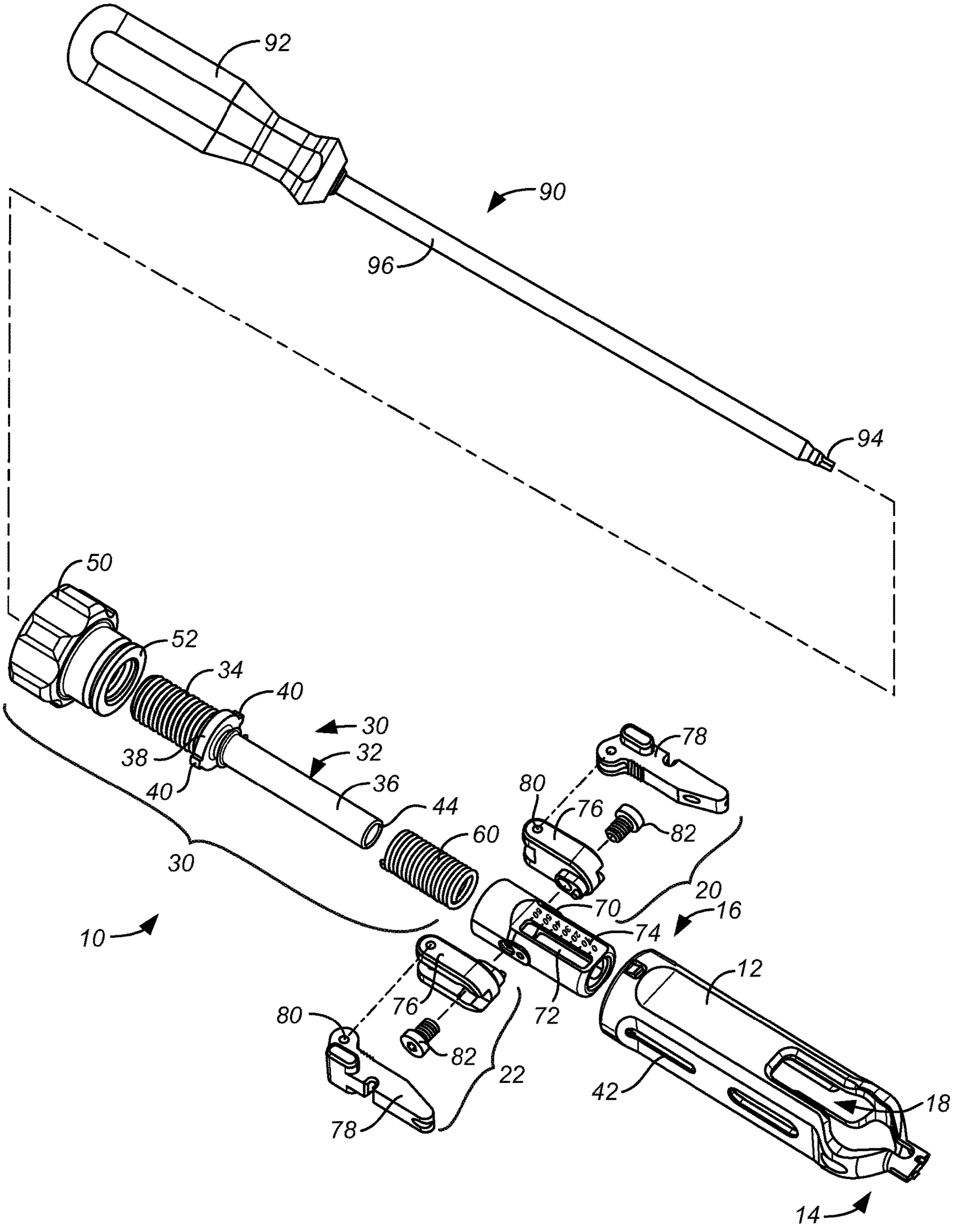
FIG. 3 is an exploded view of the graft tensioning tool of FIGS. 1 and 2 shown with portions broken away.

Referring to FIGS. 1 to 3, a graft tensioning tool 10 constructed in accordance with the principles of the present invention comprises an elongate frame 12 having a distal end 14 and proximal end 16. An axial passage 18 (best seen in FIG. 3) extends from the distal end 14 to the proximal end 16, and a pair of suture pullers 20 and 22 are slidably mounted on the sides of the elongated frame 12.

A tensioner assembly 30 is coupled to the pair of suture pullers 20 and 22 to allow a user to apply a controlled on during ligament reconstruction or other surgery, as described in more detail below. The tensioner assembly 30 typically includes a partially threaded cylinder 32 having a threaded portion 34 and a distal extension 36. A ring 38 is disposed in the middle of the partially threaded cylinder 32 between the threaded portion 34 and the distal extension 36. The ring has a pair of sliders 40, generally located on diametrically opposed sides, which are received in slots 42 in sides of the frame 12. The sliders 40 allow the partially threaded cylinder 32 to axially translate in the axial passage 18 of the elongated frame 12 while preventing rotation. In this way, a knob 50, which is rotatably mounted in the proximal end 16 of the elongated frame 12, can be used to advance and retract the partially threaded cylinder 32 within the axial passage 18. As best seen in FIG. 3, the knob 50 has an internally threaded receptacle 52 which receives the threaded portion 34 of the partially threaded cylinder 32. As the knob 50 is mounted to rotate without axial movement, rotation of the knob causes the partially threaded cylinder 32 to axially translate in either a proximal or distal direction, depending on the clockwise or counterclockwise rotation of the knob. The threads of both the receptacle 52 in threaded portion 34 and of the partially threaded cylinder 32 will be chosen to provide a relatively low ratio of translational distance to knob rotation. For example, one full rotation of the knob 50 will typically translate the partially threaded cylinder 32 by a distance in a range from 0.1 mm to 3 mm, usually from 0.5 mm to 2 mm. Such fine control of the translational distance allows control of the tension in small increments.

Axial translation of the partially threaded cylinder 32 is coupled to a puller body 70 of the tensioner assembly 30 by a spring 60. The spring 60 is typically a coil spring which is fully axially collapsed in a non-tensioned state. A proximal end of the spring 60 is attached to the partially threaded cylinder 32 on the distal side of the ring 38. A distal end of the spring 60 is attached to a proximal end of the puller body 70 so that proximal translation of the partially threaded cylinder 32 will axially tension the spring 60 causing a spring force to draw the puller body 70 in a proximal direction which in turn will draw suture pullers 20 and 22 in the proximal direction. The amount of tension applied to the puller 70 will depend on both the distance that the partially threaded cylinder 32 travels as well as the spring constant of the spring 60.

While use of a spring, such as spring 60, to transmit a proximal force to the puller body 70 is generally preferred, in other instances, the tensioner assembly 30 could be directly attached to the puller body 70 or other equivalent structure so that the suture pullers are translated directly by the tensioner assembly with a 1:1 travel ration.

The puller body 70 has a viewing slot 72 with a tension scale 74 aligned along an edge thereof. A distal end 44 of the distal extension 36 of the partially threaded cylinder 32 is visible through the viewing slot 72 and provides a marker which indicates the amount of tension being applied by the spring 60 on the tensioner assembly 30. The combination of the spring 60 and puller body 70 provides a simple spring scale which allows a user to monitor the tension applied by the tensioning tool 10 to the suture at all times during a procedure.

The suture pullers 20 and 22 typically comprise cleat bodies 76 and cleat arms 78 and are typically fixedly attached to the puller body 70 by attachment screws 82. The cleat arms 78 are attached to the cleat bodies at pivots 80, and can be moved between an open configuration, as shown in broken line in FIG. 2, and a closed configuration as shown in full line. Suture S can be passed over the cleat arm 78 the between the cleat arm and the cleat body 76, and the cleat arm can then be closed to lock the suture to the puller body 70, as shown in FIG. 2 in full line.

Figure 4A:
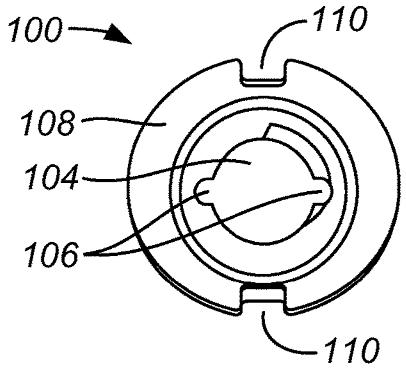
FIGS. 4A and 4B are top and side views, respectively, of an exemplary embodiment of a tunnel ring constructed in accordance with the principles of the present invention.
Figure 4B:
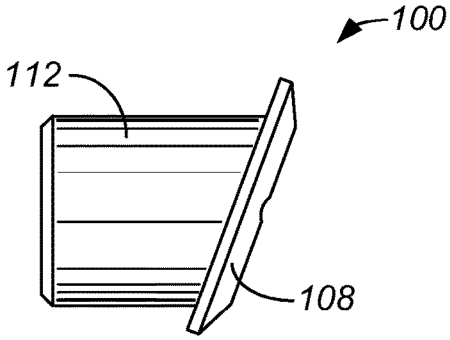

Referring now to FIGS. 4A and 4B, an exemplary tunnel ring 100 comprises a cylindrical body 112 having an opening 104 therethrough. The opening 104 is typically threaded and will have a pair of suture channels 106 running axially therethrough, typically being diametrically opposed. An upper end of the cylindrical body 112 is surrounded by a flange 108 having a pair of notches or grooves 110 formed therein. The notches 110 are configured to engage corresponding features (not shown) on the distal end 14 of the elongate frame 12 to aid in aligning and stabilizing the distal end against the tunnel ring 100 during a suture tensioning procedure, as described in greater detail below.

Figure 5A:
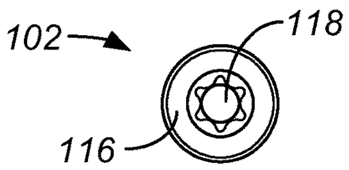
FIGS. 5A and 5B are end and side views, respectively, of an exemplary embodiment of suture lock intended for use with the tunnel ring of FIGS. 4A and 4B.
Figure 5B:
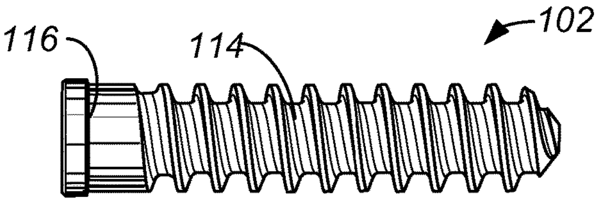
Figure 6A:
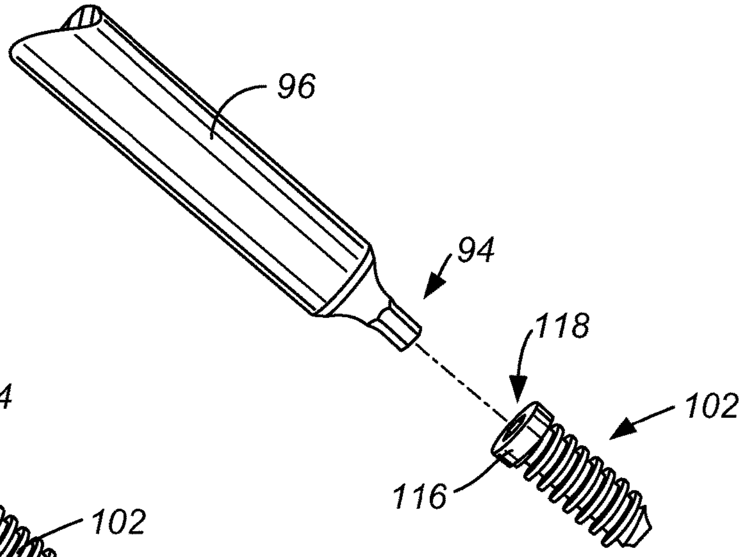
FIGS. 6A and 6B illustrate the attachment of the suture lock of FIGS. 5A and 5B to a driver tip of an attachment tool in accordance with principles of the present invention.

Referring now to FIGS. 5A and 5B, an exemplary suture lock 102 comprises a threaded shaft 114 and a drive head 116. The drive head 116 includes a mating feature 118 configured to receive and rotatably couple to the distal driver tip 94 of the locking tool 90. As further shown in FIGS. 6A, a hexagonal driver tip 94 may be detachably introduced into the mating feature, a hexagonal receptacle 118, on the driver head 16 so that the locking tool 90 can be used to both advance the suture lock 102 and to rotate (screw) the suture lock through the tunnel ring 100 and into a bone tunnel, as described in more detail below. It will be appreciated that many other coupling features could be employed.

Figure 7:
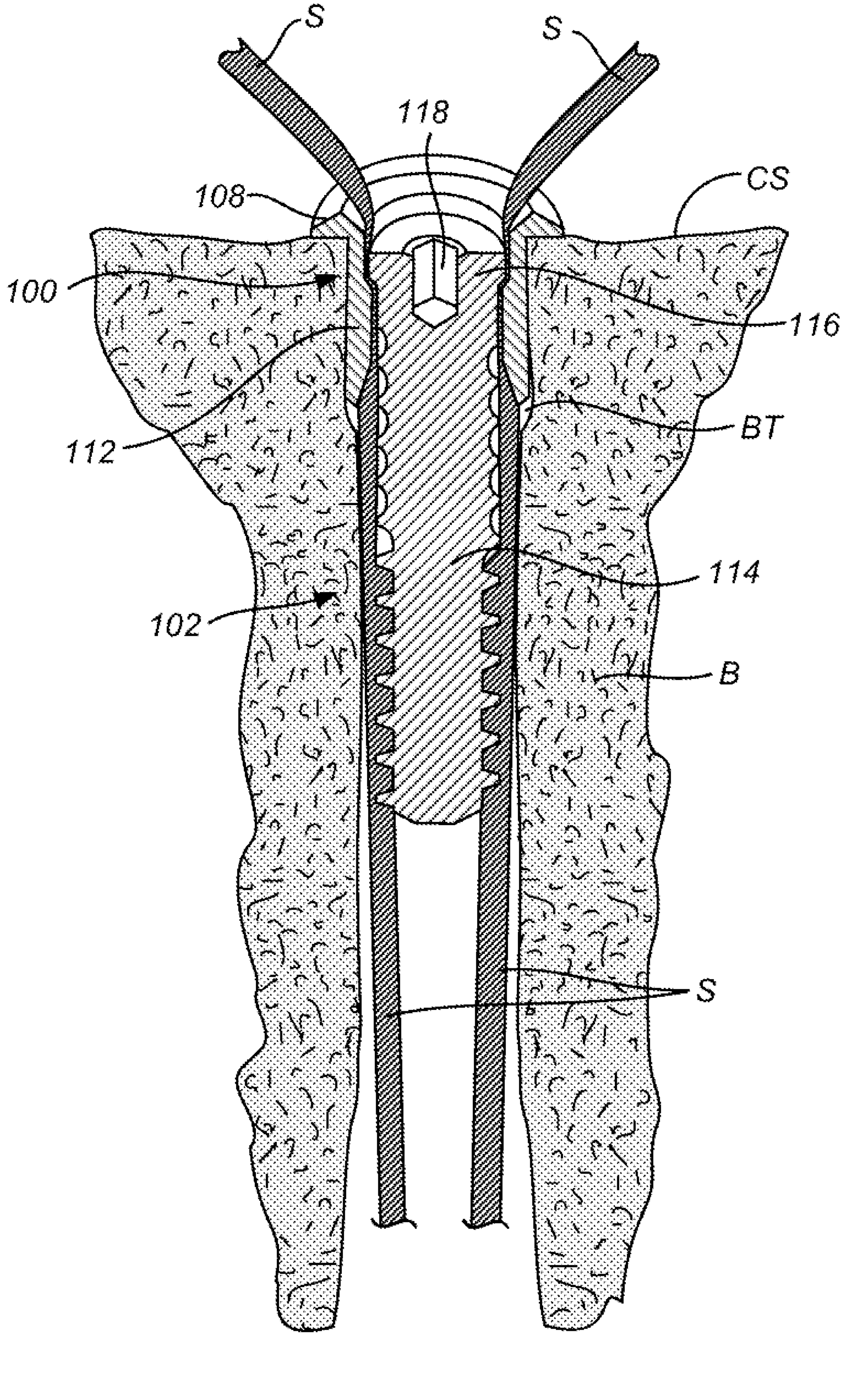
FIG. 7 illustrates the placement of the tunnel ring and suture lock of the previous figures in a bone tunnel to lock suture in place.

Referring now to FIG. 7, placement of the suture lock 102 through the tunnel ring 100 and into a bone tunnel BT is shown to capture a pair of suture ends S which emerge upwardly through the bone tunnel and are attached at a lower end (not shown) to a graft or other soft tissue prosthesis. A portion of each suture end S is captured between an outer peripheral surface of the drive head 116 and an inner surface of the opening 104 in the tunnel ring 100. The clearance between the drive head and the opening is limited, assuring that the suture is tightly held. The threaded shaft 114 extends downwardly into the bone tunnel BT and further immobilizes the suture ends as well as threadably engaging the tunnel walls to anchor both the tunnel ring 100 the suture lock 102 in place.

Figure 8:
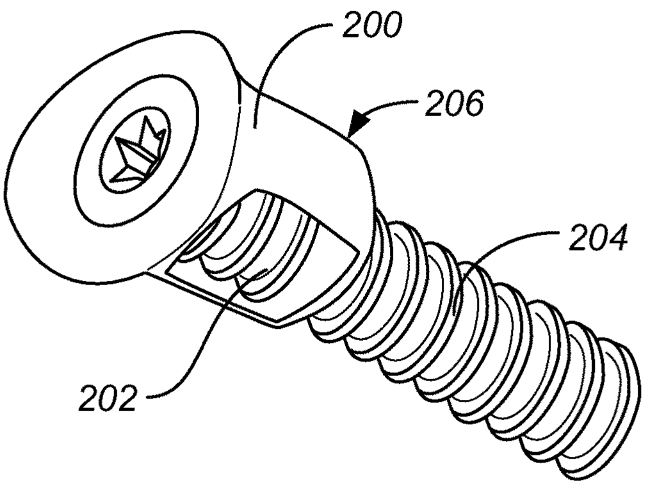
FIG. 8 illustrates an alternative embodiment of a combination tunnel ring and suture lock constructed in accordance with the principles of the present invention.
Figure 9:
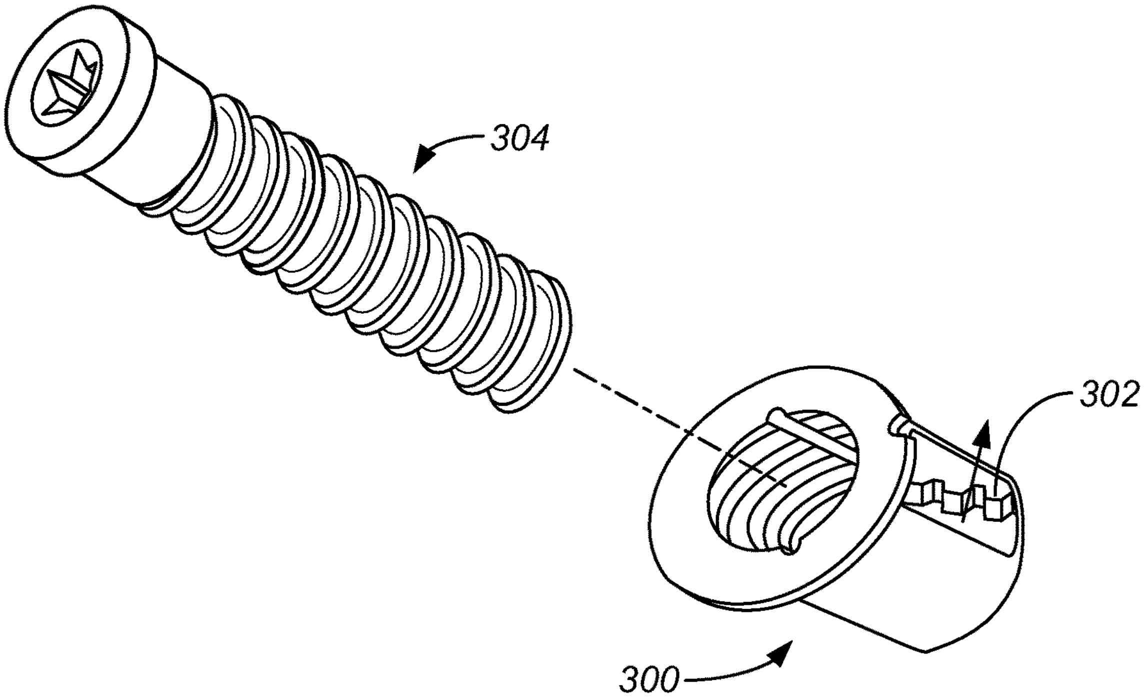
FIG. 9 illustrates a second alternative embodiment of a combination tunnel ring and suture lock constructed in accordance with the principles of the present invention

Other embodiments of suture ring-suture lock combinations are shown in FIGS. 8 and 9. A threaded shaft 204 in FIG. 8 is similar to previously described threaded shaft 114, while tunnel ring 200 differs from tunnel ring 100 as it includes a pair of windows 200 on the side of a cylindrical body 206. The windows 200 allow the graft to directly contact the bone tunnel and increase the surface area for graft incorporation.

FIG. 9 illustrates a shorter suture ring-suture lock combination where threaded shaft 304 has a length approximately equal to the length of the tunnel ring 300. As the threaded shaft 304 does not extend into the bone tunnel, spring locks 302 are provided to engage cortical bone at the opening into the bone tunnel to both stabilize and immobilize the tunnel ring 300 after implantation. Typically, the spring locks 302 will expand in an outwardly radial direction, as shown by the arrow, when the threaded shaft 304 is advanced in the suture ring. When in the expanded configuration, the spring locks provide further axial and rotational stability of the tunnel ring 300 during tensioning and further construct stability after locking.

Figure 10A:
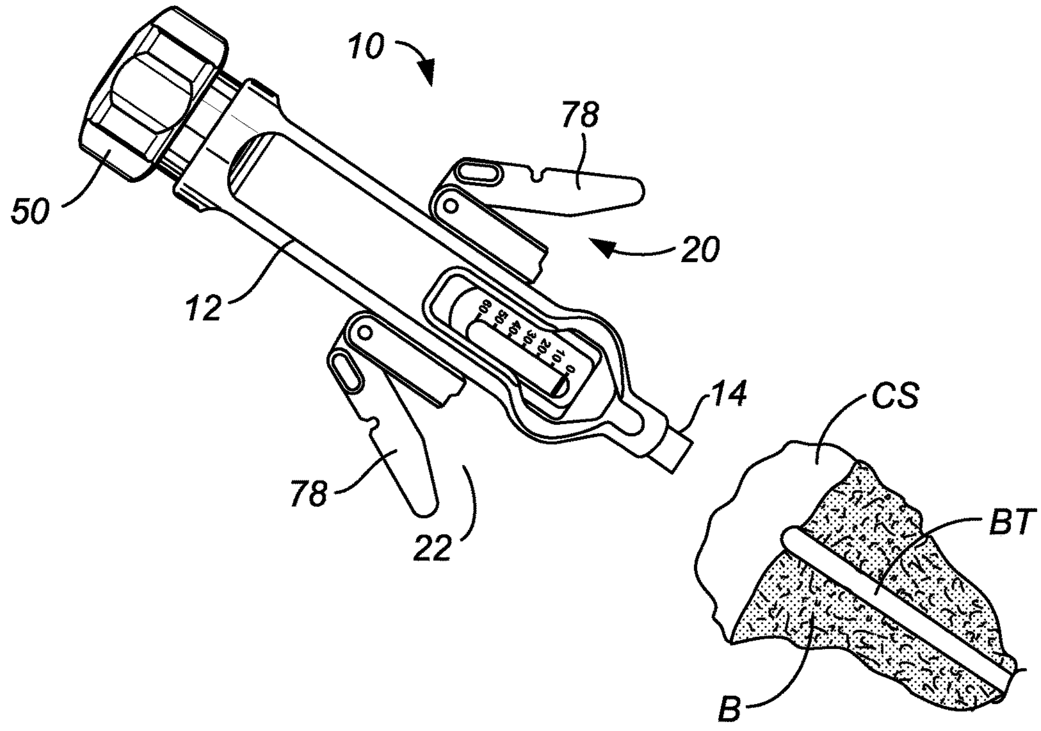
FIGS. 10A to 10D illustrate use of the tensioning and locking tools of the present invention for tensioning and fixating a pair of suture ends emerging from a bone tunnel in cortical bone.
Figure 10B:
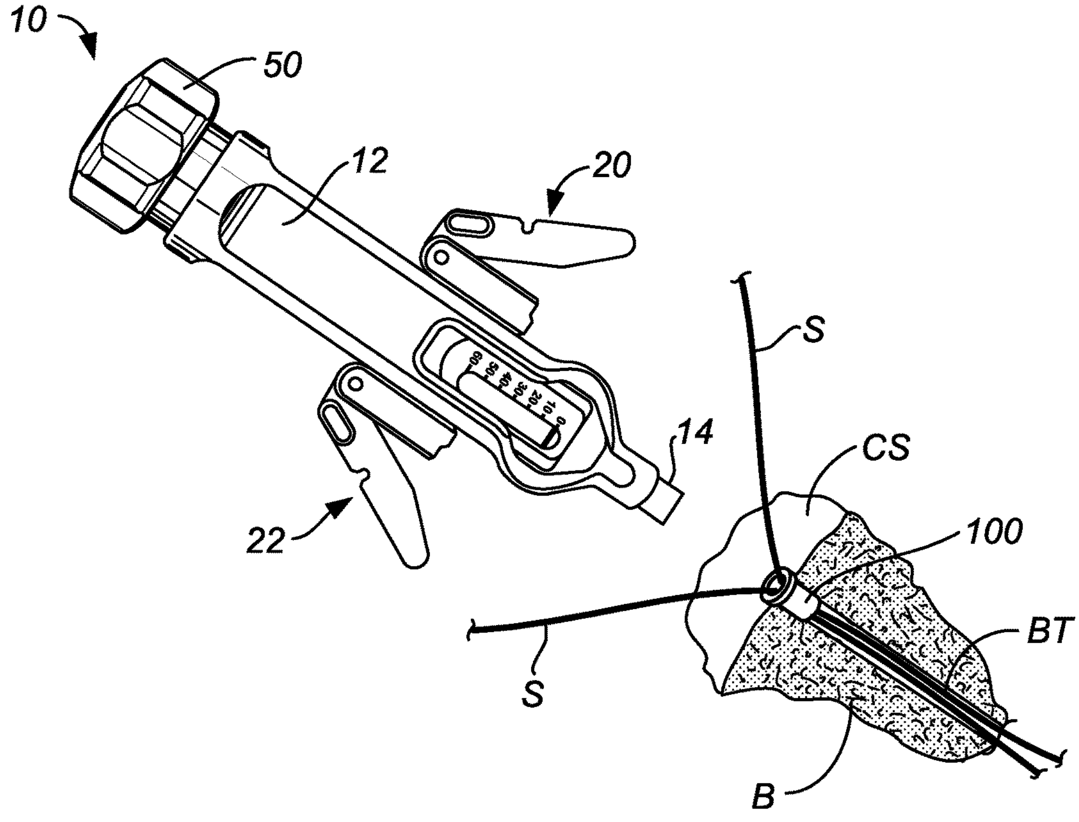
Figure 10C:
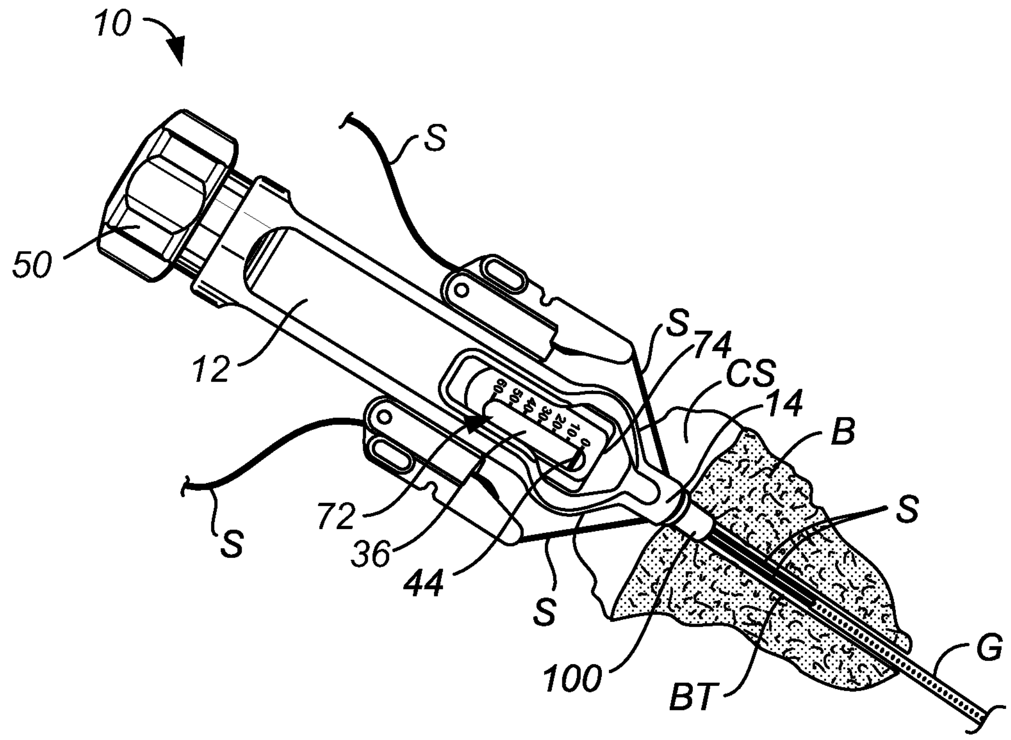

Referring now to FIGS. 10A to 10D, use of the graph insertion tool 10 of the present invention for tensioning and fixating a pair of suture ends S will be described. The tensioning tool 10 initially has the cleat arms 78 open, as shown in FIG. 10A, and is brought to the site of a bone tunnel BT. Tunnel ring 100 may then be placed in an opening the bone tunnel BT, and suture ends pulled through the bone tunnel and tissue ring, as shown in FIG. 10B. The sutures are then threaded through the suture pullers 22, and the cleat arms 78 are closed to secure the suture ends S, as shown in FIG. 10C. Before closing the cleat arms 78, the suture ends S will be lightly tensioned to remove slack before tensioning. The suture pullers 20 and 22 on the tensioning tool 10 may then be translated proximally to apply a target tension to the suture, usually simultaneously but in some embodiments the pullers may be modified to allow separate tensioning.

Figure 6B:
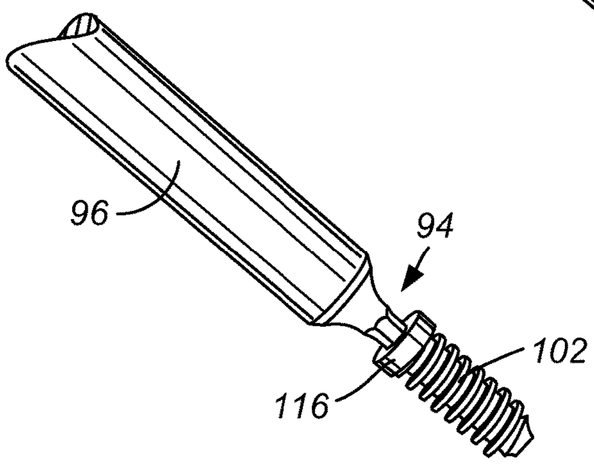
Figure 10D:
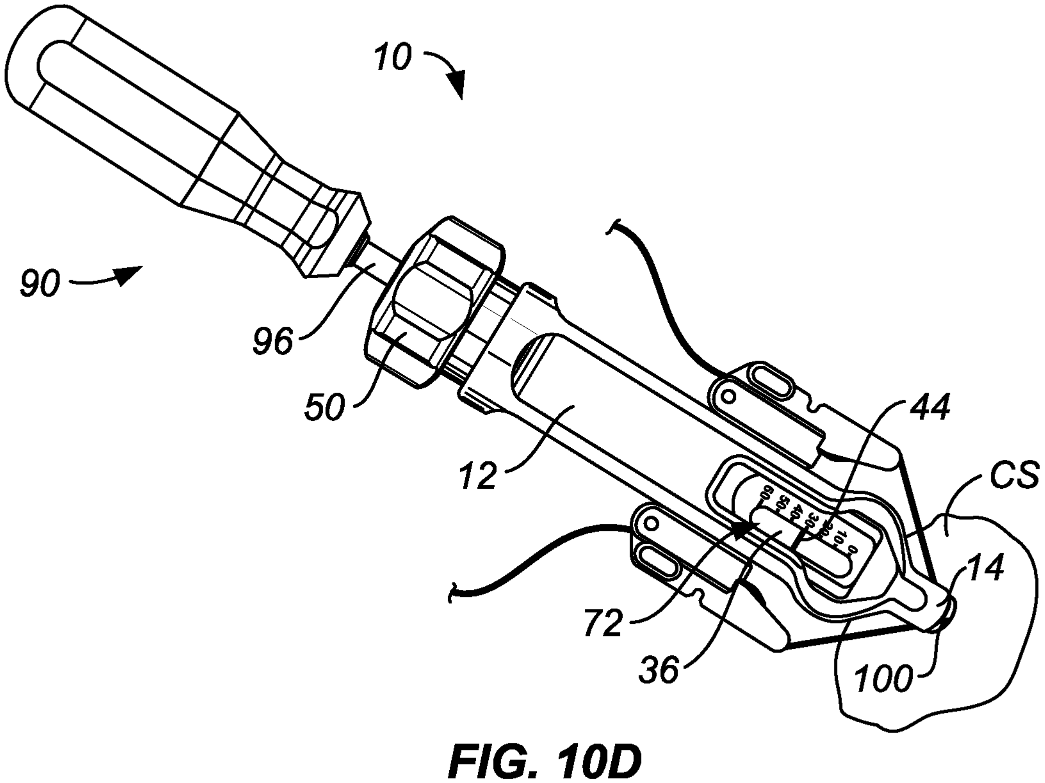

At this point in the procedure, the distal end 44 the distal extension 36 of the partially threaded cylinder 32 will be at the 0 marker on the scale 74. The knob 50 may then be rotated to draw the pullers 20 and 22 proximally, applying tension to the sutures as indicated on the scale 74. When the distal end 44 is observed to reach a desired tension level as indicated on the tension scale 74. When a target tension is achieved, rotation of the knob 50 may be stopped and tensioning of suture left at the target level, as shown in FIG. 10D. At this point, the tension on the suture ends S will remain fixed, allowing the user to advance a suture lock through the axial passage 18 (FIG. 2) of the elongate frame of the tensioning tool using the locking tool 90, as shown FIG. 6B. The locking tool 90 may then be manually rotated to drive the threaded shaft 114 of the suture lock 102 through the tunnel ring 100 and into the bone tunnel BT, as shown in FIG. 7.

Alternatively, the suture lock 102 may be loosely placed into the suture ring 100 prior to tensioning of the suture, and the locking tool 90 used only to heighten a suture lock after the desired suture tension has been achieved. In either case, use of the separate locking tool to advance and/or lock suture lock in place allows the target tension to be maintaining with minimal or no variation.

Figure 11:
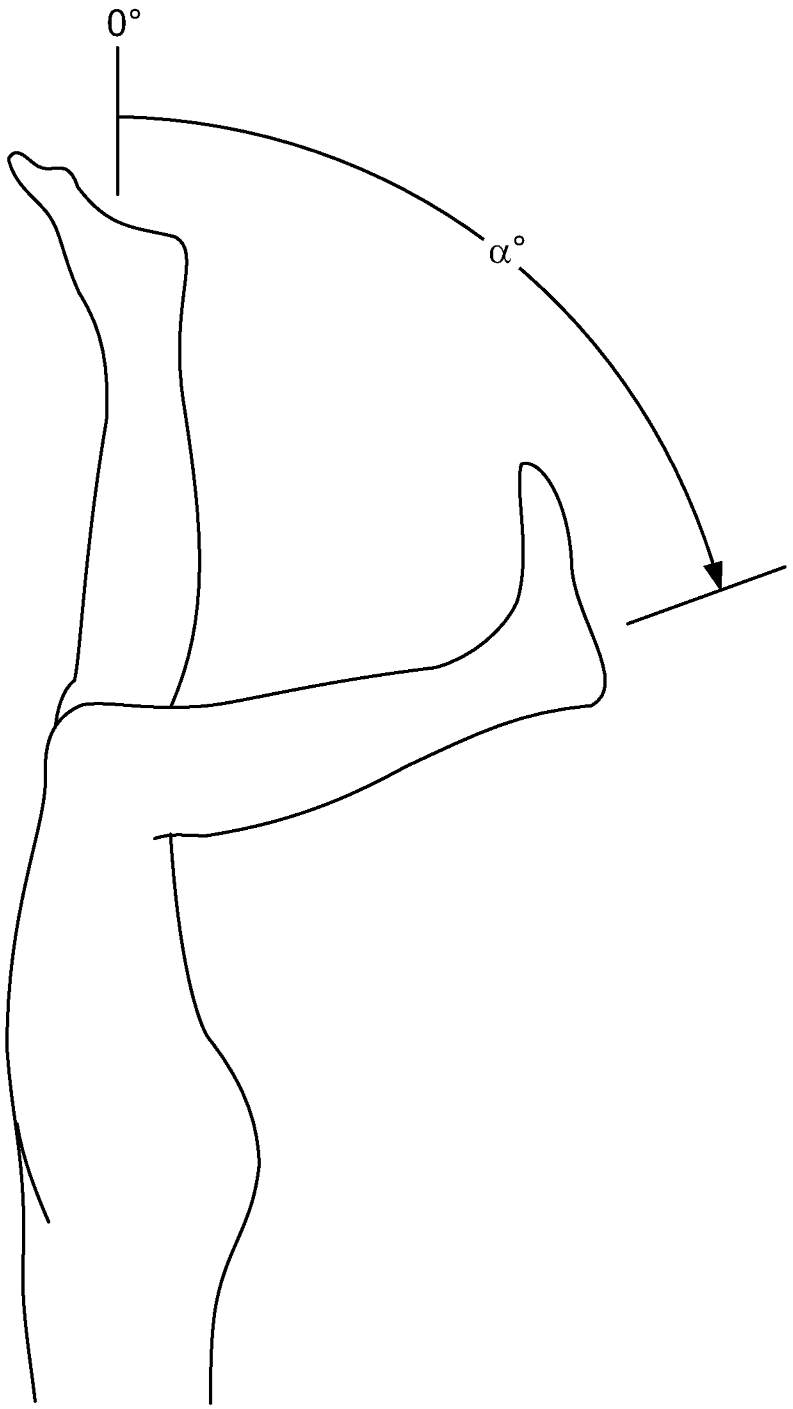
FIG. 11 illustrates flexion of a knee during ligament reconstructive surgery of the knee.
Figure 12A:
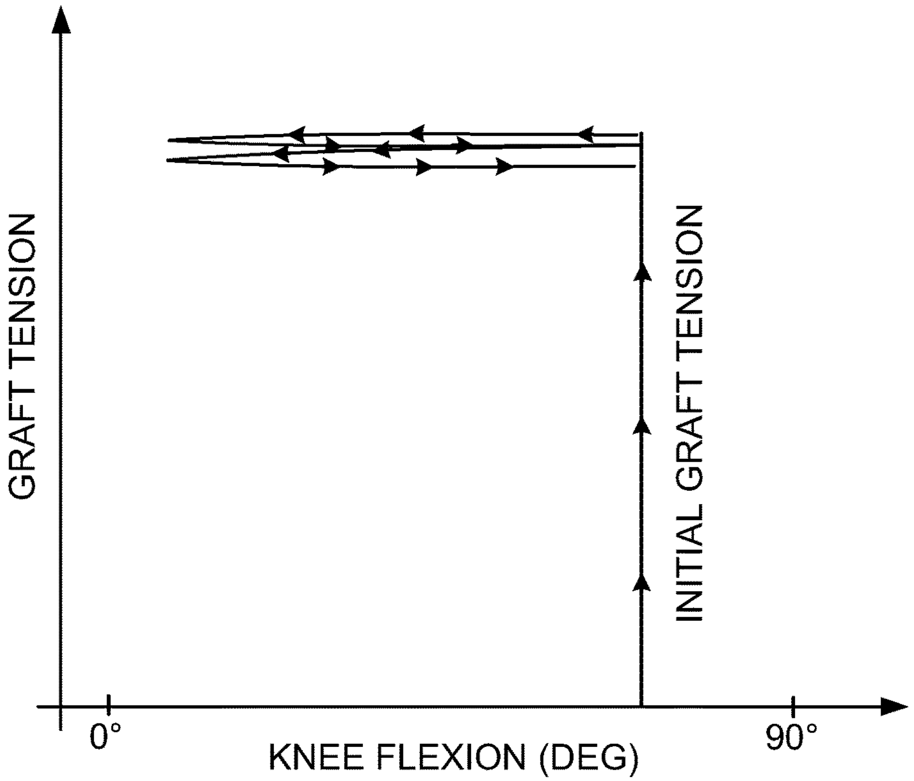
FIGS. 12A and 12B illustrate plots of flexion versus graft tension which may be generated using the graft tensioning tool of the present invention during knee ligament surgery.
Figure 12B:
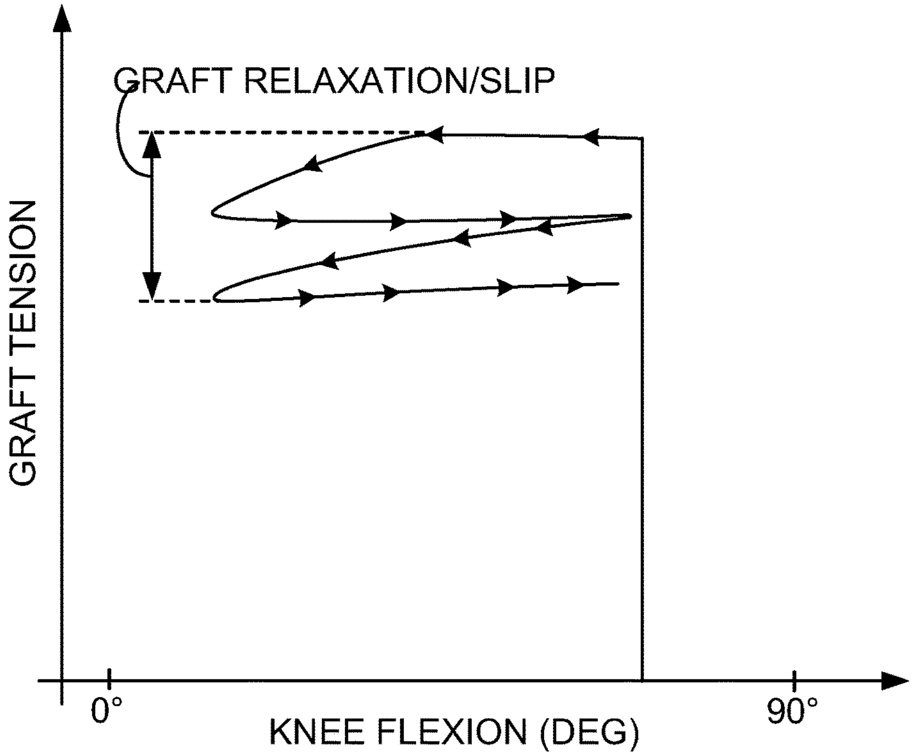

The graft tensioning tools 10 of the present invention may be used to check graft tension in the knee or other joint while the joint is moved through different degrees of flexion. As shown in FIG. 11, the knee they be moved through different flexion angles $\alpha$ while the suture remains tensioned by the graft tensioning tool 10, as shown for example in FIG. 10C. The degree of flexion may be measured using a conventional instrument, such as a goniometer, but is preferably measured using an embedded tilt sensor, such as an electrolytic tilt sensor. The flexion angle and tension may thus be recorded for a range of knee flexions, for example from 0° to 90°. By plotting the measured graph against knee flexion, as shown in FIGS. 12A and 12B, the quality of the graft implantation and degree of tensioning may be determined. In some instances, when the graft tensioning tool 10 has a digital tension measurement output as well as a digital flexion angle output, such plots may be automatically generated and presented on a display and/or printed by a printer plotter.

Such plots can be useful for determining the outcome of an implementation. As shown in FIG. 12A, for example, if graph tension remains substantially constant over the number of flexion cycles, the graft is stable and the tension appropriate. In contrast, as shown in FIG. 12B, if the tension lessens over repeated cycles, the graft is likely unstable and/or the graph tension is inappropriate.

While preferred embodiments of the present invention have and the opening shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention methods and structures within the scope of these claims and their equivalents be covered thereby.

What is claimed is:

1. A graft tensioning tool for use with a tunnel ring and a suture lock operable to be received within an opening of the tunnel ring, the graft tensioning tool comprising:
- an elongate frame having a proximal end, a distal end, and a passage extending proximally from the distal end, wherein the distal end is configured to detachably engage the tunnel ring;
- a first suture puller and a second suture puller, each suture puller movably mounted to the elongate frame and configured to detachably engage a length of suture;
- a tensioner on the elongate frame, the tensioner configured to displace the first and second suture pullers in a proximal direction relative to the elongate frame; and
- a tension gauge coupled to the tensioner to measure tension applied by the tensioner to the first and second suture pullers; and
- a locking tool configured to engage the suture lock through the passage of the frame when the distal end of the frame engages the tunnel ring.

2. The graft tensioning tool of claim 1, wherein the first suture puller is disposed on a first side of the elongate frame and the second suture puller is disposed on a second side of the elongate frame.

3. The graft tensioning tool of claim 1, wherein the tensioner is configured to displace the first and second suture pullers simultaneously.

4. The graft tensioning tool of claim 1, wherein the locking tool is configured to carry the suture lock through the passage of the frame and position the suture lock in the opening in the tunnel ring.

5. The graft tensioning tool of claim 1, wherein the distal end of the elongate frame comprises an opening configured to circumscribe the tunnel ring.

6. The graft tensioning tool of claim 5, wherein the tunnel ring has a lower surface configured to engage bone and an upper surface and wherein the opening of the elongate frame is configured to circumscribe the upper surface of the tunnel ring.

7. The graft tensioning tool of claim 5, wherein the opening is configured to interlock with the upper surface of the tunnel ring.

8. The graft tensioning tool of claim 5, further comprising an interlock including a protrusion on the opening of the distal end of the elongate frame and a recess on an exterior surface of the tunnel ring, wherein the protrusion is configured to engage the recess when the opening circumscribes the tunnel ring.

9. The graft tensioning tool of claim 1, wherein the first and second suture pullers each comprise a cleat.

10. The graft tensioning tool of claim 1, wherein the first and second suture pullers are mounted on a carriage that is slidably disposed in a distal portion of the passage in the frame, wherein the suture pullers are exposed through slots in the frame.

11. The graft tensioning tool of claim 10, wherein the tensioner comprises a shuttle assembly coupled to the carriage, and wherein the shuttle assembly is configured to be retracted to proximally displace the carriage.

12. The graft tensioning tool of claim 11, wherein the shuttle assembly is configured to be manually retracted.

13. The graft tensioning tool of claim 11, wherein the shuttle assembly comprises an externally threaded cylinder and an internally threaded knob,
- wherein the knob is rotatably mounted on the frame at a fixed axial position and the threaded cylinder is slidably mounted in the passageway of the frame but prevented from rotating, and
- wherein a proximal portion of the threaded cylinder is received in a distal portion of the knob so that manual rotation of the knob will proximally retract the threaded cylinder.

14. The graft tensioning tool of claim 13, further comprising a spring coupling the threaded cylinder to the puller carriage.

15. The graft tensioning tool of claim 14, wherein the tension gauge is coupled to the spring to provide a tension readout based upon elongation of the spring.

16. The graft tensioning tool of claim 1, further comprising a tilt sensor configured to measure joint flexion and a display,
- wherein the tilt sensor has a digital output,
- wherein the tension gauge comprises a load cell transducer having a digital output, and
- wherein the digital display is configured to display a plot of flexion angle versus tension.

17. The graft tensioning tool of claim 16, further comprising a wireless transmitter connected to the load cell and the tilt sensor for transmission to a remote digital display.

18. The graft tensioning tool of claim 16, wherein the load cell is wired to a digital display on the elongate frame.

19. The graft tensioning tool of claim 1, wherein the locking tool comprises a shaft with a proximal handle and a distal end configured to detachably engage the suture lock.

20. A graft tensioning system comprising:
- the graft tensioning tool of claim 1;
- the tunnel ring; and
- the suture lock.

21. The graft tensioning system of claim 20, wherein the tunnel ring comprises a shoulder washer.

22. The graft tensioning system of claim 21, wherein the shoulder washer has a pair of interior channels on an interior surface for receiving and guiding the suture lengths.

23. The graft tensioning system of claim 22, wherein the interior surface is threaded.

24. The graft tensioning system of claim 20, wherein the suture lock comprises a threaded shaft that can be rotatably advanced into the tunnel ring to compress and lock the suture and/or a graft implant.

25. The graft tensioning tool of claim 1, wherein the tensioner is configured to apply a continuously variable tension.

26. The graft tensioning tool of claim 1, wherein the tensioner is configured to displace the first and second suture pullers in both a proximal direction and a distal direction relative to the elongate frame.

27. The graft tensioning tool of claim 1, wherein the passage extends through the frame from the distal end to the proximal end.

28. A surgical tensioning tool configured for use with a tunnel ring, the surgical tensioning tool comprising:

a frame having a proximal end, an open distal end, and a longitudinal passage extending proximally from the open distal end;

a first suture puller and a second suture puller, wherein each suture puller is movably mounted to the frame and is configured to detachably engage a corresponding and respective suture portion;

a tensioner mounted to the frame and configured to displace the first and second suture pullers in a proximal direction relative to the frame; and a tension gauge configured to measure tension applied by the tensioner to the first and second suture pullers;

wherein, with the open distal end engaged with the tunnel ring, an opening of the tunnel ring is accessible via the longitudinal passage.

29. The surgical tensioning tool of claim 28, wherein the longitudinal passage extends fully through the frame to the proximal end.

30. The surgical tensioning tool of claim 28, wherein the open distal end comprises a protrusion operable to engage a notch of the tunnel ring to thereby prevent rotation of the tunnel ring relative to the frame.

31. The surgical tensioning tool of claim 28, wherein the tensioner is configured to displace the first and second suture pullers simultaneously.

32. A system comprising the surgical tensioning tool of claim 28, the system further comprising:

the tunnel ring; and a suture lock configured to threadedly engage the tunnel ring.

33. The system of claim 32, wherein the tunnel ring is configured to rotationally interlock with the open distal end.

34. The system of claim 32, further comprising a locking tool configured to extend through the longitudinal passage to facilitate rotation of the suture lock relative to the tunnel ring.

35. A surgical tensioning system, comprising:

a tunnel ring configured for insertion into a bone tunnel;

a suture lock operable to be threaded into the tunnel ring;

a surgical tensioning tool, comprising:

a frame having a proximal end, an open distal end, and a longitudinal passage extending proximally from the open distal end, wherein the open distal end is operable to rotationally interlock with the tunnel ring;

a pair of suture pullers movably mounted to the frame, wherein each suture puller is operable to detachably engage a corresponding and respective suture portion;

a tensioner mounted to the frame and configured to displace the pair of suture pullers proximally relative to the frame; and a tension gauge configured to measure tension applied by the tensioner to the pair of suture pullers; and a locking tool operable to extend through the longitudinal passage to facilitate manipulation of the suture lock within the tunnel ring.

36. The surgical tensioning system of claim 35, wherein the tunnel ring comprises a notch; and wherein the open distal end comprises a protrusion operable to engage the notch to thereby rotationally interlock the tunnel ring and the frame.

37. The surgical tensioning system of claim 35, wherein the open distal end is configured to circumferentially surround a proximal portion of the tunnel ring.

38. The surgical tensioning system of claim 35, wherein the tensioner is configured to displace the first and second suture pullers simultaneously.

39. The surgical tensioning tool of claim 35, wherein the longitudinal passage extends fully through the frame to the proximal end.

* * * * *